United States Patent
Perry et al.

(10) Patent No.: US 6,439,446 B1
(45) Date of Patent: Aug. 27, 2002

(54) SAFETY LOCKOUT FOR ACTUATOR SHAFT

(76) Inventors: Stephen J. Perry, 151 Great Rd., Shirley, MA (US) 01464; Roy H. Sullivan, III, 23 Meaghan Way, Millville, MA (US) 01529; Eric K. Litscher, 1 John Matthew Rd., Hopkinton, MA (US) 01748

(*) Notice: Subject to any disclaimer, the term of this patent is extended or adjusted under 35 U.S.C. 154(b) by 49 days.

(21) Appl. No.: 09/726,490

(22) Filed: Dec. 1, 2000

(51) Int. Cl.⁷ .............................................. A61B 17/068
(52) U.S. Cl. ...................................... 227/175.2; 227/19
(58) Field of Search ................................ 227/19, 175.2, 227/175.1, 175.3, 176.1, 181.1, 179.1

(56) References Cited

U.S. PATENT DOCUMENTS

| | | | |
|---|---|---|---|
| 4,289,133 A | * 9/1981 | Rothfuss | 227/175.3 |
| 4,319,576 A | * 3/1982 | Rothfuss | 227/19 |
| 4,612,933 A | * 9/1986 | Brinkerhoff et al. | 227/175.2 |
| 5,762,255 A | * 6/1998 | Chrisman et al. | 227/19 |
| 5,799,857 A | * 9/1998 | Robertson et al. | 227/175.2 |
| 6,050,472 A | * 4/2000 | Shibata | 227/179.1 |

* cited by examiner

*Primary Examiner*—Scott A. Smith
(74) *Attorney, Agent, or Firm*—Fay Kaplun & Marcin LLP

(57) ABSTRACT

A safety lock-out to prevent rotation of a rotary actuator is described. When an axial distance between a first and a second portion of an actuated mechanism exceeds a selected distance, the lock-out prevents the rotation. The safety lock-out includes a shaft rotatably connected to the first portion and axially movable relative to the second portion. A locking member is adapted to lock the rotary actuator by placing a protrusion in a notch of the shaft, thus preventing rotation of the shaft. The device also includes a spring member urging the locking member in the locking position, and an unlocking member adapted to urge the locking member in the unlocked position when the selected distance is not exceeded.

28 Claims, 5 Drawing Sheets

SAFETY LOCKOUT FOR ACTUATOR SHAFT

BACKGROUND OF THE INVENTION

Embodiment of the present invention are related to a safety lockout to prevent rotation of an actuator when a selected distance between two portions of an actuated mechanism is exceeded. In particular, the safety lockout prevents rotation of the actuator shaft of a Full Thickness Resectioning Device (FTRD) by locking the shaft when the distance between the anvil and the stapling head of the FTRD exceeds a selected distance.

DESCRIPTION OF RELATED ART

An FTRD is a device that is used to endoscopically remove lesions, growths or other tissue samples from a body cavity of a patient. Typically this cavity can be the rectum or a lower part of the intestine. During the operation of the device, a distal end of the FTRD is inserted in the cavity, and is oriented so that an opening formed in the distal end faces the tissue to be removed. Various devices can then be used to grasp the tissue and to partially pull it inside the FTRD. The surgeon operating the FTRD can then activate a stapler device disposed at the distal end of the FTRD, and staple the region surrounding the tissue sample so that it can be removed without excessive bleeding or the incision becoming too large.

Once the stapling is complete, the surgeon can activate the knife that cuts around the tissue, so the growth or lesion can be removed. The staples keep the surrounding tissue in position so the incision can heal more easily.

The stapler device is located in the head of the FTRD, and is generally activated by an actuating shaft operated by the surgeon from the proximate end of the FTRD. As the shaft rotates, staples are fired by the stapling mechanism, so that the surgeon can control where and when to fire the staple. The staple is fired from a stapling head portion of the stapler device, so that the prongs of the staple go through the tissue, and then are bent back by the anvil portion of the stapler device. The anvil bends and shapes the prongs of the staples, so that they hold the layers of tissue together.

While positioning the stapler device, the anvil and the stapling head can be moved axially relative to each other, so that the layers of tissue can be positioned in the gap between the two parts. The anvil is then moved closer to the stapling head to immobilize the tissue in a position suitable for stapling. If the anvil portion is not at the correct distance from the stapling head portion when the surgeon activates the stapler device, the staple's prongs can be bent in an unsatisfactory shape, resulting in a less than ideal hold by the staple of the layers of tissue.

Conventional devices can have indicators to show to the surgeon whether the correct gap to form a satisfactory staple is reached, but it is up to the surgeon to check the gap before activating the stapler device. These systems also are subject to errors because of the distance between the stapler device and the gap indicator.

SUMMARY OF THE INVENTION

Exemplary embodiments of the present invention are directed to a safety lockout to prevent rotation of a rotary actuator of an FTRD that substantially obviates one or more of the problems due to limitations and disadvantages of the related art. Additional features of the invention will be set forth in the description which follows, and in part will be apparent from the description, or may be learned by practice of the invention.

To achieve these and other advantages and in accordance with the invention as embodied and broadly described, the invention is a safety lock-out to prevent rotation of a rotary actuator when an axial distance between a first and a second portion of an actuated mechanism exceeds a selected distance. The safety lock-out includes a shaft rotatably connected to the first portion, axially movable relative to the second portion, and defining a notch. A locking member adapted to lock the rotary actuator is included, that is movable between a locking position and an unlocked position. The locking member fits in the notch when in the locking position thus preventing rotation of the shaft. The device also includes a spring member urging the locking member in the locking position and an unlocking member adapted to urge the locking member in the unlocked position when the selected distance is not exceeded.

In another aspect, the invention is a locking mechanism to prevent rotation of an actuating shaft of a Full Thickness Resectioning Device, that includes a frame rotatably supporting the shaft and coupled to a stapling head of the Full Thickness Resectioning Device, and a yoke coupled to an anvil of the Full Thickness Resectioning Device, movable axially relative to the frame. The device also includes a locking member movable relative to the shaft between a locking position and an unlocked position, the locking member engaging a notch in the shaft to prevent rotation of the shaft when in the locking position. Also included is an unlocking member adapted to move the locking member to the unlocked position when an axial distance between the anvil and the stapling head is less than a selected distance.

It is to be understood that both the foregoing general description and the following detailed description are exemplary and explanatory, and are intended to provide further explanation of the invention as claimed.

BRIEF DESCRIPTION OF THE DRAWINGS

The accompanying drawings are included to provide further understanding of embodiments of the present invention, are incorporated in and constitute a part of the specification, and illustrate embodiments of the invention.

In the drawings.

DETAILED DESCRIPTION OF EMBODIMENTS OF THE INVENTION

Figure 1:
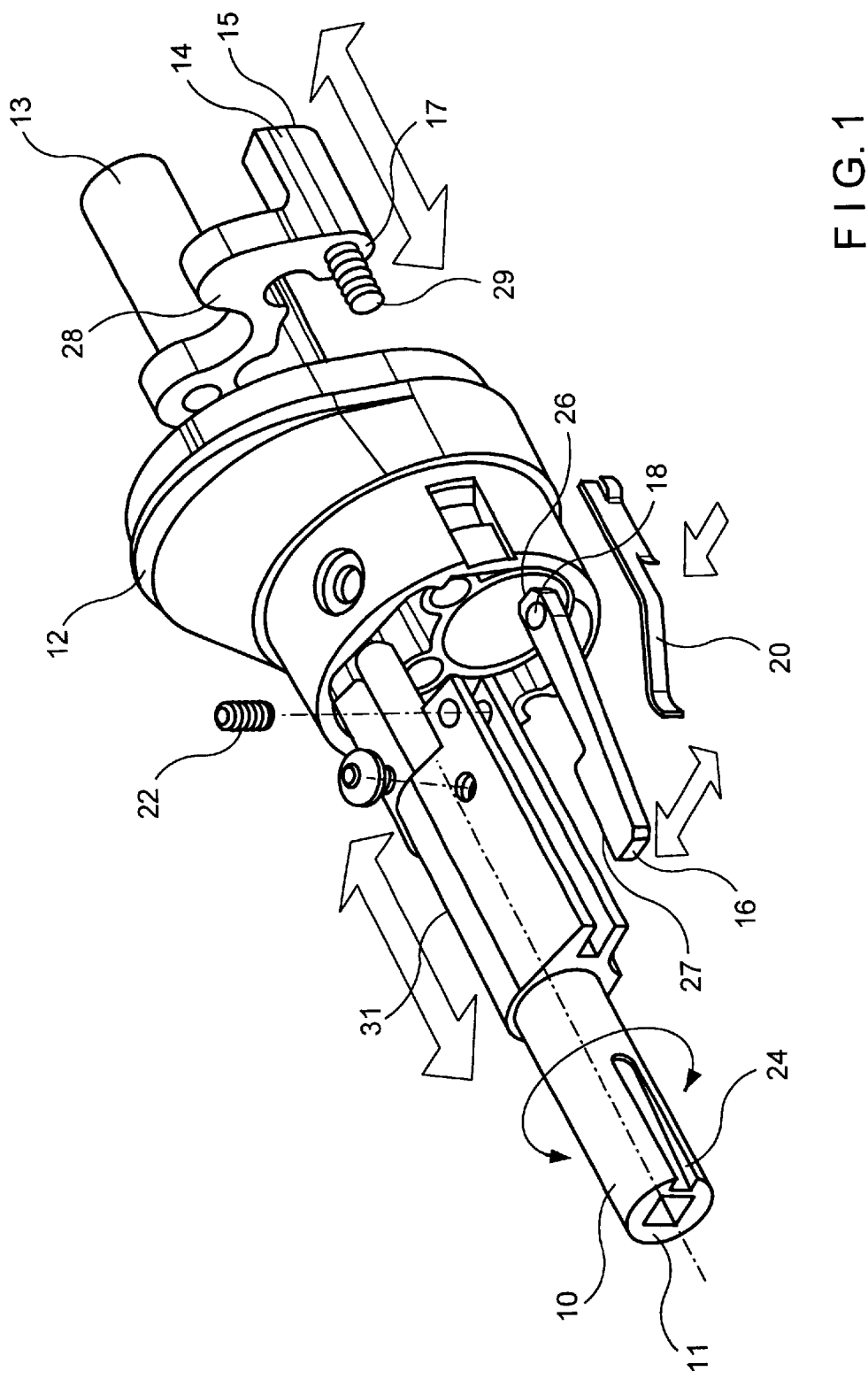
FIG. 1 is a perspective view showing one embodiment of the safety lockout according to the present invention.

FIG. 1 shows an embodiment of the safety lockout according to the present invention, used to prevent rotation of a actuating shaft of a Full Thickness Resectioning Device. This assembly is located at a distal end of the FTRD, and forms part of the head section of the FTRD. A shaft 10 extends through the distal head section of the FTRD, and can be connected at end 11 to a flexible drive shaft (not shown) extending to the proximate end of the FTRD. Shaft 10 also has another end 13 that extends into a stapling head portion of the FTRD, not shown in the drawing, from which the staples are propelled into the tissue.

The surgeon operating the device can remotely rotate shaft 10 so that the mechanism of the stapling head connected to end 13 of shaft 10 fires a staple into the tissue when a sufficient rotation of shaft 10 has occurred. A frame 12 supports shaft 10 so that it can rotate and, if necessary, translate within frame 12. In one embodiment, frame 12 can be the rear tail cap of the head of the FTRD.

A yoke 14 is used in an embodiment of the safety lockout, and is connected at end 15 to the anvil portion of the device, not shown in the drawing. As explained above, the anvil is used as a back stop for the staples, to control folding of the prongs of the staple after the prongs pierce the tissue to be stapled. The axial gap between the anvil connected to end 15 of yoke 14 and the stapling head connected to end 13 of shaft 10 is adjustable. The gap is widened to permit introduction of the tissue between the two components, and then the gap is reduced so that the prongs of the staple can be properly folded by the anvil. To accomplish this, yoke 14 is movable axially with respect to shaft 10, as shown by the large arrow in FIG. 1. This movement can be effectuated, for example, by threaded worm gears 29 attached to face 17 of yoke 14, or by other elongated rods or cables extending from face 17 of yoke 14 to a control area at the proximate end of the FTRD.

The surgeon operating the FTRD can rotate shaft 10 and can translate yoke 14, both located at the distal end of the device, by manipulating controls placed at the proximate end of the FTRD device. In particular, the surgeon can translate yoke 14 so that the gap distance between the anvil and the stapling head is increased or reduced as required. When the gap is reduced to the required specified value, the surgeon can rotate shaft 10 to cause the stapling head to fire a staple through the tissue and into the anvil. In one embodiment of the invention, the specified distance separating the anvil and the stapling head can be between approximately 0.066 and 0.09 inches. In another embodiment, the gap can be of about 0.066 inches. This selected distance can vary depending on the size of the staples, but for staples of a given size, the selected distance should be maintained, so that the staples will have the desired shape after being fired.

To prevent shaft 10 from rotating, thus firing a staple, when the gap distance is greater than the selected distance, this exemplary embodiment includes a notch 24 formed in shaft 10, and a lever 16 pivotally mounted on frame 12 with a pivot 18. Lever 16 can be moved radially with respect to shaft 10, as shown by the arrow in FIG. 1. Lever 16 can have a unlocked position, away from shaft 10, where it does not interfere with rotation of shaft 10. Lever 16 can also have a locking position where it is pivoted towards shaft 10 until protrusion 27 fits inside of notch 24, and prevents rotation of shaft 10.

In one exemplary embodiment, lever 16 is urged in the locking position by a spring 20, attached to frame 12. A guide 31 can also be used to help direct protrusion 27 of lever 16 into notch 24. Lever 16 is one example of a locking member that can be used together with spring member 20 to immobilize rotation of shaft 10 when such rotation is not desirable. Other shapes and configurations of the locking member can also be successfully utilized, such as a spring loaded catch, a pivotable member of different shape, etc.

The safety lockout according to this embodiment can also include an unlocking member used to move lever 16 of the locking member into the unlocked position. For example, lever 16 can have a cam surface 26 formed at one end, which can be activated to pivot lever 16 into the unlocked position by moving protrusion 27 out of notch 24. A cam actuating surface 28 can be formed on yoke 14, so that when yoke 14 approaches within a certain distance of frame 12, cam actuating surface 28 contacts cam surface 26, and continued movement of yoke 14 towards lever 16 results in lever 16 moving to the unlocked position.

Since yoke 14 is coupled to the anvil portion of the stapler, and lever 16 is coupled to the stapling head portion of the stapler via shaft 10, axial movement of the anvil relative to the stapling head results in proportional axial movement of yoke 14 relative to lever 16. This movement can be calibrated so that when the axial distance between the anvil and the stapling head is reduced to less than a selected distance, cam actuator surface 28 of yoke 14 enters in contact with the cam surface 26 of lever 16, and allows the rotation of shaft 10.

In the context of this description, the term "coupled" refers to a connection that can be either direct or through linkages, and that results in movement of one element proportionally to the movement of a second element. For example, yoke 14 is coupled to the anvil of the stapler, so that when the anvil moves relative to the stapling head, the yoke also moves relative to the lever 16 by an amount proportional to the movement of the anvil.

According to an exemplary embodiment of the invention, lever 16 of the locking member can be adjusted axially so that cam surface 26 will contact cam actuator 28, to move lever 16 to the unlocked position, when the distance between the anvil and the stapling head is reduced to the selected distance. In one example, the axial adjustment can be made using a offset fastener 22, that can be a screw or an axle, and that can have an offset so that lever 16 is moved axially as the fastener 22 is rotated.

Figure 2:
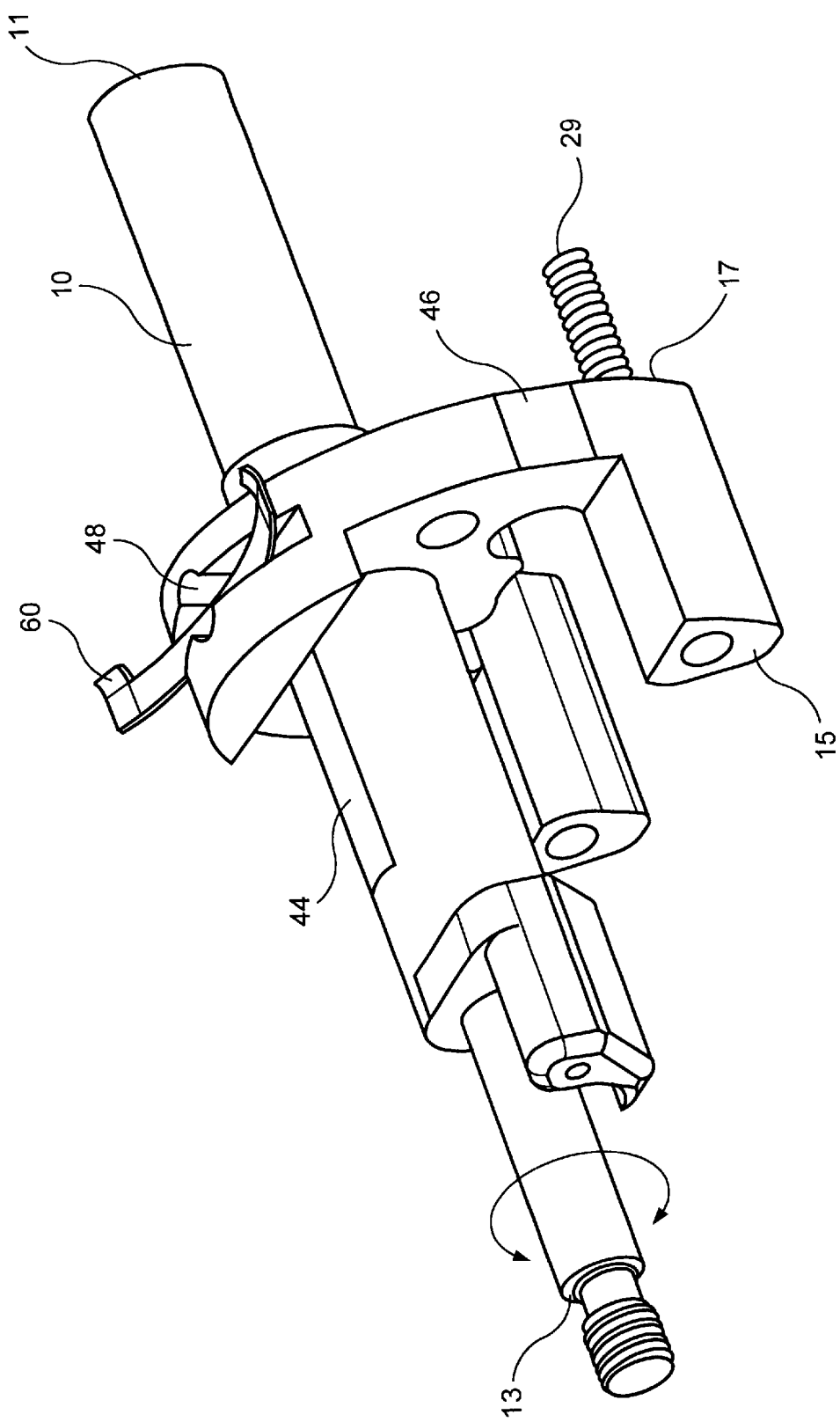
FIG. 2 is a perspective view showing a second embodiment of the safety lockout according to the present invention.
Figure 3:
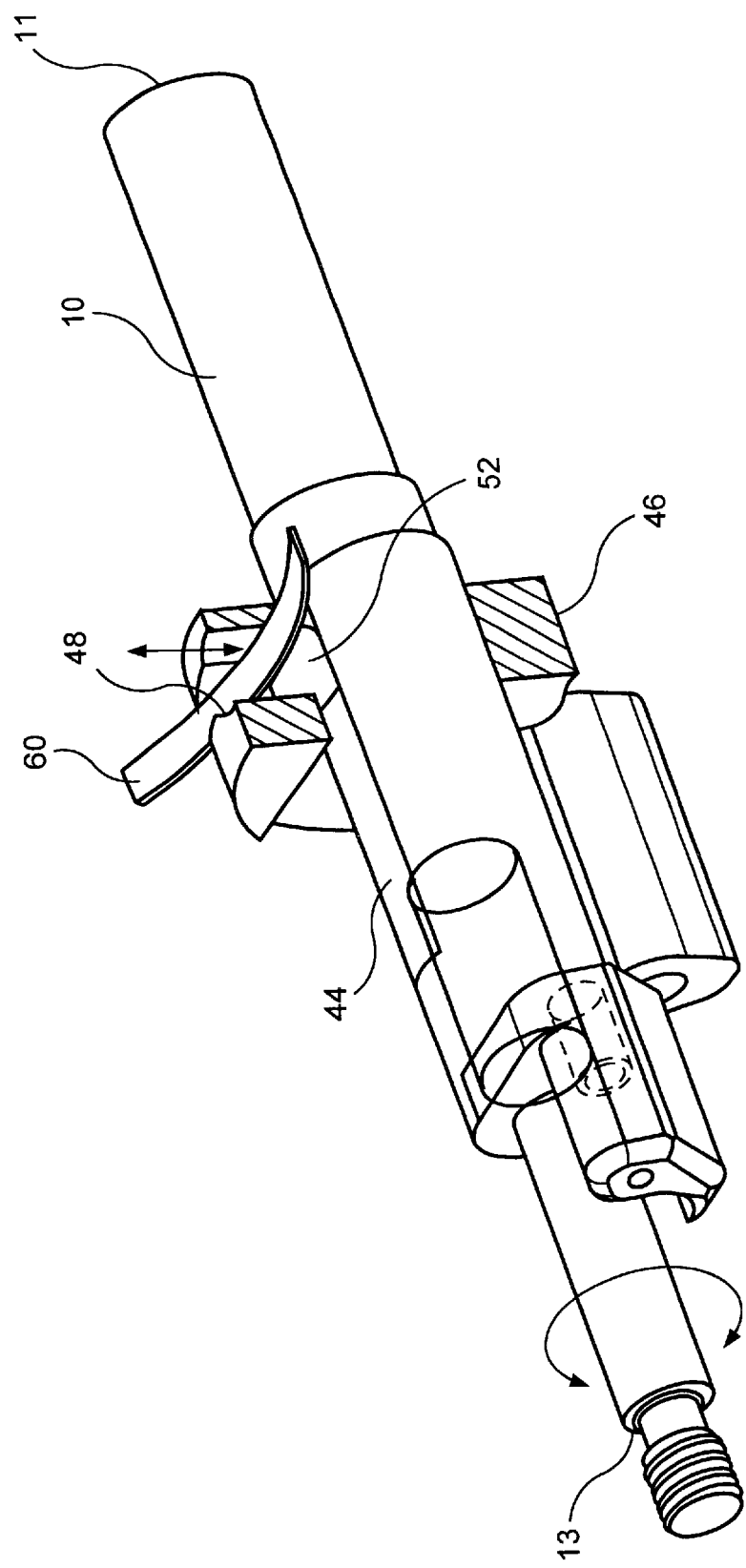
FIG. 3 is a cut-away perspective view showing a detail of the safety lockout shown in FIG. 2.

FIG. 2 shows another embodiment of the safety lockout according to the invention that includes an over-center spring. As described before, shaft 10 is connected at end 11 to a control module (not shown) at the proximal end of the FTRD, and at end 13 is connected to the stapling head portion of the stapler. A yoke 46 is coupled at end 15 to the anvil of the stapler (not shown), and at end 17 is connected to actuators 29 to translate the anvil and the yoke combination in an axial direction. In this manner, yoke 46 can be translated axially relative to shaft 10.

A cut out 48 can be formed in yoke 46, in which over-center spring 60 is disposed and is connected to a ball bearing 52. In this embodiment, ball bearing 52 forms part of the locking member, and can move between a unlocked position radially removed from shaft 10, and a locking position in which ball bearing 52 fits inside of a groove 44 formed in shaft 10. Cut out 48 in yoke 46 can be shaped so that it prevents ball bearing 52 from moving in a direction tangent to the shaft 10, so that when bearing 52 is inside of groove 44, shaft 10 is prevented from rotating. Spring 60 can be attached to yoke 46 in a conventional manner, not shown in the drawing, and can urge ball bearing 52 into the locking position to prevent shaft 10 from rotating. Ball bearing 52 can also have a different shape, such as, for example, a polygonal notch, an elongate protrusion, or any other shape adapted to prevent rotation of shaft 10.

As the distance between the anvil and the stapling head changes, yoke 46 and shaft 10 also axially translate relative to one another, since they are coupled respectively to the anvil and the stapling head. Accordingly, when the distance between the stapling head and the anvil is reduced to less than the selected distance, a mechanism can be provided to move ball bearing 52 to the unlocked position, so that rotation of shaft 10 is allowed. For example, one edge of gap 44 in shaft 10 can push ball bearing 52 upwards, overcoming the force of spring 60, and moving ball bearing 52 outside of gap 44.

Figure 4:
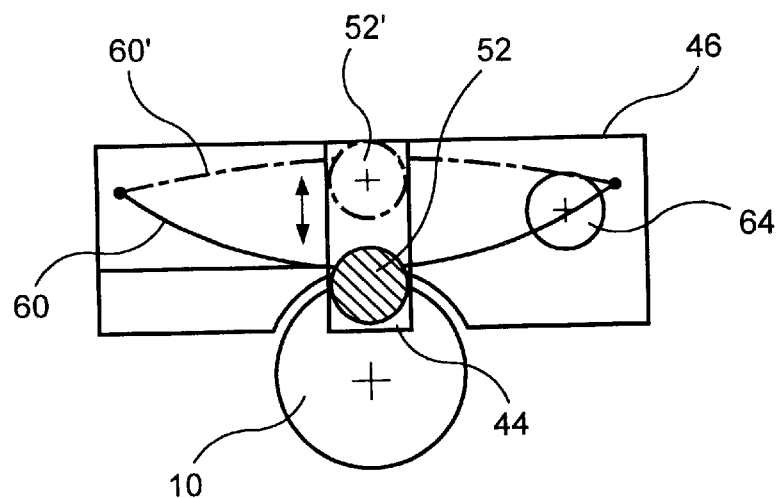
FIG. 4 is a front elevation view showing a detail of the embodiment shown in FIG. 2.
Figure 5:
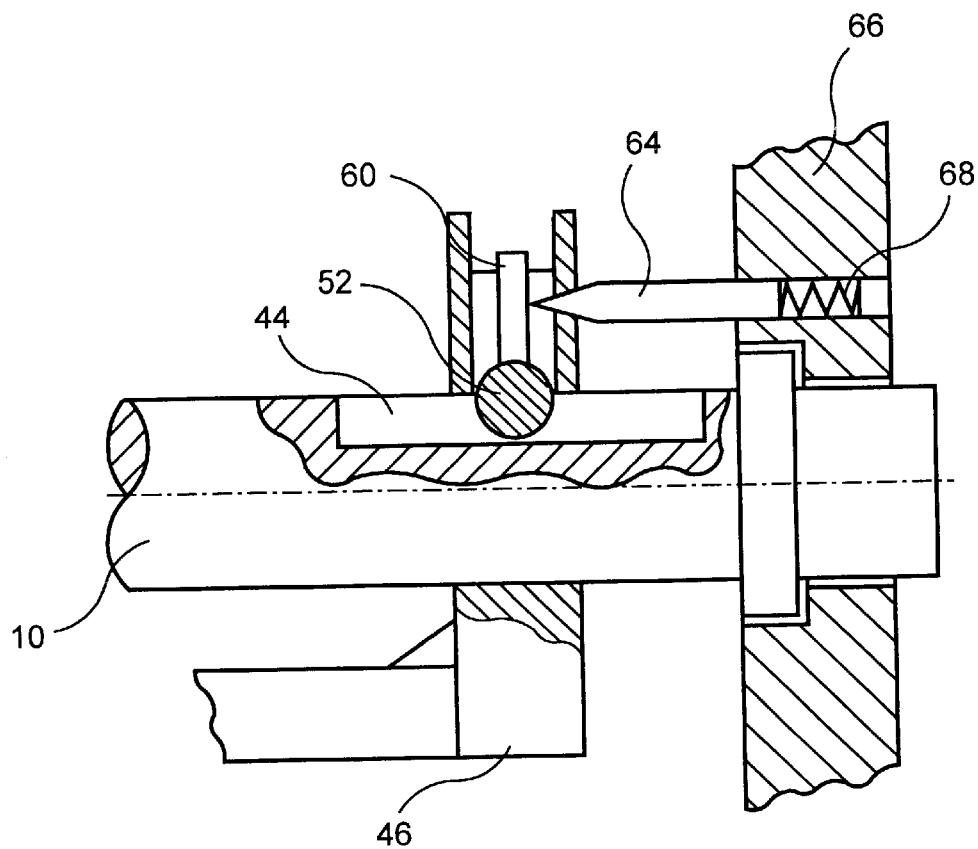
FIG. 5 is a side view showing an embodiment of the safety lockout including an adjustable trigger.

In this exemplary embodiment, the spring member can include a bistable spring 60 that has two states, one state corresponding to the locked position of the locking member and another state corresponding to the unlocked position of the locking member. As shown in FIG. 4, the first state of spring 60 corresponds to ball bearing 52 being urged into groove 44 of shaft 10. A second state is shown in dashed lines, where spring 60' pulls ball bearing 52' in a position away from shaft 10. The configuration of the spring element according to this exemplary embodiment is such that spring 60 is only stable in one of the two states described above, and only a small force needs to be applied to spring 60 to switch it from one state to another. This force can be provided, for example, by a pin 64 extending from a support 66 that is connected to the shaft 10, shown in FIG. 5.

As the distance between support 66 and spring 60 changes, reflecting a change of position between the anvil coupled to yoke 46 and the stapling head coupled to shaft 10, pin 64 approaches or moves away from spring 60. When spring 60 is in the state where ball bearing 52 is preventing shaft 10 from rotating, movement of the anvil towards the stapling head causes pin 64 to approach spring 60. The tip of pin 64 can be shaped so that when it touches spring 60 is pushes it away from shaft 10, causing it to jump to the other stable state where ball bearing 52 is in the unlocked position.

In this embodiment, the unlocking member includes the pin or trigger 64, the support 66 which can be attached to frame 12, and can include a treaded portion 68 that allows axial adjustment of the position where pin 64 triggers the change of state of spring 60.

The configuration of the embodiment shown in FIGS. 2 through 5 permits a very rapid change from the locking position to the unlocked position of the locking member, reducing greatly the dwell time in which the shaft 10 is not fully locked by bearing 52, but is also not fully free to rotate. This also results in more precisely preventing the shaft 10 from rotating when the gap between the anvil and the stapling head is too large.

Figure 6:
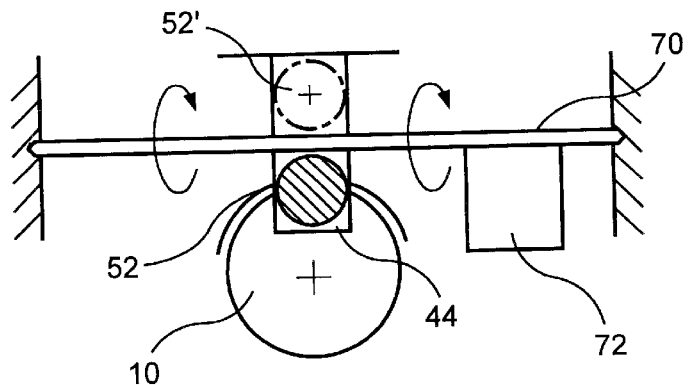
FIG. 6 is a front view showing an embodiment of the safety lockout including an actuating tab.

FIG. 6 shows a different exemplary embodiment of the safety lockout, where a ball bearing 52 is attached to a bistable actuating shaft 70 having an actuating tab portion 72. In this embodiment, shaft 70 rotates so that in one position ball bearing 52 fits inside gap 44 of shaft 10, thus preventing the rotation of shaft 10, and in a second position ball bearing 52' is rotated away from shaft 10. A pin similar to pin 64 shown in FIG. 5 can be used to push on paddle 72, thus causing shaft 70 to rotate from the locking position to an unlocked position. A bi-stable spring of known design can be used to maintain shaft 70 in one of the two stable positions.

Figure 7:
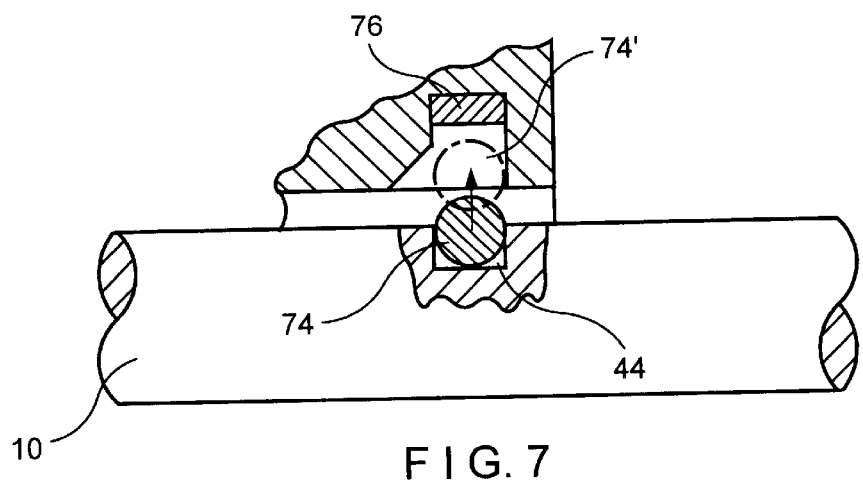
FIG. 7 is a side view showing an embodiment of the safety lockout including a magnet.

Additional methods and configurations to obtain a bi-stable actuation of the locking member can be devised within the scope of the invention. FIG. 7 shows an exemplary embodiment where a ball bearing 74 moves in and out of groove 44 in shaft 10 in response to actuation of a magnet 76. Magnet 76 moves axially relative to shaft 10, and can be calibrated to lift ball bearing 74 to a position 74' when the gap between the anvil and the stapling head is less than the selected distance.

Figure 8:
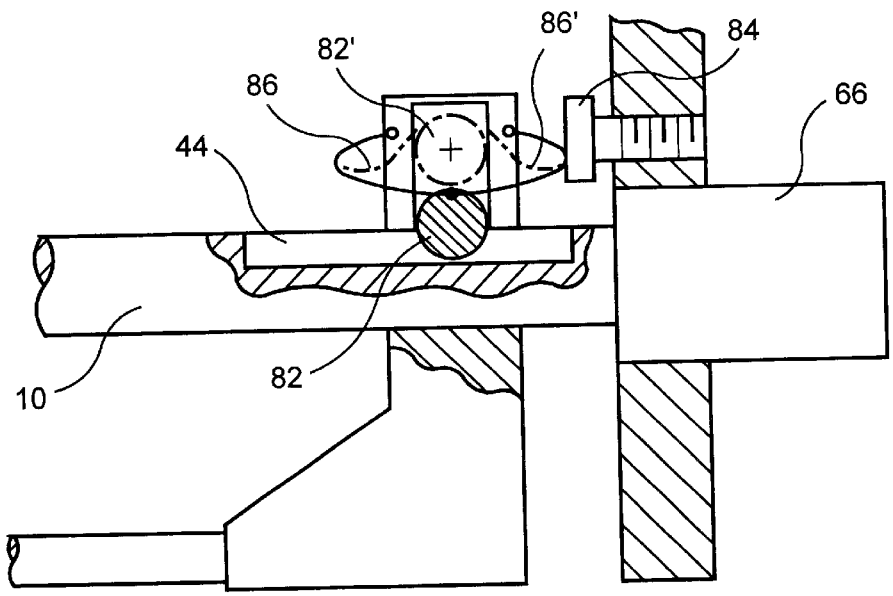
FIG. 8 is a side view showing an embodiment of the safety lockout that includes a bellows spring.

FIG. 8 shows yet another exemplary embodiment according to the invention, where the spring member includes a bellows spring 86, that has one stable position where ball 82 is placed inside gap 44 of shaft 10, and another stable position where ball 82' is moved away from shaft 10, thus allowing it to rotate. The transition between the two stable positions is accomplished by bumping bellows spring 86 with a bumper 84, to cause the bellows spring 86 to move from the locking position state to the unlocked position state. Bumper 84 can be a threaded bolt or similar device that allows adjustment of the location where the spring is tripped, so that it will correspond to a gap between the anvil and the stapling head equal to the selected distance.

It will be apparent to those skilled in the art that modifications and variations can be made in the structure of the embodiments of the present invention, without departing from the spirit or scope of the invention. Thus, it is intended that the present invention encompasses the modifications and variations of these embodiments provided they come within the scope of the appended claims and their equivalents.

What is claimed is:

1. A safety lock-out to prevent rotation of a rotary actuator when an axial distance between a first and a second portion of an actuated mechanism exceeds a selected distance, comprising:
   a shaft rotatably connected to the first portion, axially movable relative to the second portion, said shaft defining a notch;
   a locking member adapted to lock the rotary actuator, said locking member being movable between a locking position and an unlocked position, wherein the locking member fits in the notch when in the locking position thus preventing rotation of the shaft;
   a spring member urging the locking member in the locking position; and
   an unlocking member adapted to urge the locking member in the unlocked position when the selected distance is not exceeded.

2. The lock-out according to claim 1, further comprising a yoke connected to the second portion, the yoke being movable axially relative to the shaft.

3. The lock-out according to claim 1, wherein the locking member is a lever pivotable relative to the shaft between the locking and the unlocked positions.

4. The lock-out according to claim 3, wherein the unlocking member comprises a cam surface formed on the lever and a cam actuator coupled to the second portion, the cam surface and cam actuator cooperating to urge the lever in the unlocked position when the axial distance is less than the selected distance.

5. The lock-out according to claim 4, wherein the cam actuator comprises a shaped surface of a yoke connected to the second portion, the yoke being movable axially relative to the lever.

6. The lock-out according to claim 1, wherein the actuated mechanism is a stapler portion of a full thickness resectioning device, and the first and second portions are one of a stapling head actuated by the shaft and an anvil.

7. The lock-out according to claim 1, wherein the spring member is a leaf spring extending from a frame supporting the shaft.

8. The lock-out according to claim 1, wherein the spring member is a bistable spring, having a state corresponding to the locking position, and another state corresponding to the unlocked position.

9. The lock-out according to claim 8, wherein the locking member is a protrusion extending from the bistable spring.

10. The lock-out according to claim 9, wherein the bistable spring is disposed on a yoke movable axially relative to the shaft, the yoke being connected to the second portion.

11. The lock-out according to claim 8, wherein the unlocking member comprises a trigger to trip the bistable spring from the locking position state to the unlocked position state.

12. The lock-out according to claim 11, wherein the trigger is an elongated member extending from a frame supporting the shaft.

13. The lock-out according to claim 12, wherein the elongated member is adjustable axially to trip the bistable spring when the axial distance is substantially equal to the selected distance.

14. The lock-out according to claim 8, wherein the bistable spring is a leaf spring.

15. The lock-out according to claim 8, wherein the bistable spring is a bellows spring.

16. The lock-out according to claim 1, wherein the unlocking member is adjustable axially to urge the locking member in the unlocked position when the selected distance is not exceeded.

17. The lock-out according to claim 16, wherein the selected distance is between about 0.066 in. and 0.09 in.

18. A locking mechanism to prevent rotation of an actuating shaft of a Full Thickness Resectioning Device, comprising:
   a frame rotatably supporting the shaft and coupled to a stapling head of the Full Thickness Resectioning Device;
   a yoke coupled to an anvil of the Full Thickness Resectioning Device, movable axially relative to the frame;
   a locking member movable relative to the shaft between a locking position and an unlocked position, the locking member engaging a notch in the shaft to prevent rotation of the shaft when in the locking position; and
   an unlocking member adapted to move the locking member to the unlocked position when an axial distance between the anvil and the stapling head is less than a selected distance.

19. The locking mechanism according to claim 18, further comprising an actuator to urge the locking member in one of the locking position and unlocked position.

20. The locking mechanism according to claim 19, wherein the actuator is a bistable spring.

21. The locking mechanism according to claim 20, wherein the locking member is a protrusion extending from the bistable spring.

22. The locking mechanism according to claim 20, wherein the bistable spring is disposed on the yoke, and the unlocking member comprises a trigger linked to the frame, adapted to trip the bistable spring to an unlocked position state when the axial distance is less than the selected distance.

23. The locking mechanism according to claim 18, wherein the locking member is a lever pivotable relative to the shaft.

24. The locking mechanism according to claim 23, wherein the unlocking member comprises a cam actuator formed on the yoke, the cam actuator and a cam surface formed on the lever cooperating to pivot the lever to the unlocked position when the axial distance between the anvil and the stapling head is less than the selected distance.

25. The locking mechanism according to claim 23, wherein the lever is axially adjustable to move to the unlocked position when the axial distance between the anvil and the stapling head does not exceed the selected distance.

26. The locking mechanism according to claim 18, wherein the anvil is axially movable relative to the stapling head, and the yoke is movable proportionally to movement of the anvil.

27. The locking mechanism according to claim 18, wherein the unlocking member comprises an elongate protrusion axially movable relative to the locking member, a distance between the elongate protrusion and the locking member being proportional to the distance between the anvil and the stapling head.

28. The locking mechanism according to claim 18, wherein the selected distance ween about 0.066 in. and 0.09 in.

* * * * *